(12) United States Patent
Hummel et al.

(10) Patent No.: US 7,368,292 B2
(45) Date of Patent: May 6, 2008

(54) DIFFERENTIAL REFLECTION SPECTROSCOPY SYSTEM AND METHOD FOR DETECTING EXPLOSIVES AND OTHER TARGET MATERIALS

(75) Inventors: Rolf E. Hummel, Gainesville, FL (US); Ann Marie Fuller, Gainesville, FL (US); Claus Schollhorn, Gainesville, FL (US); Paul H. Holloway, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 11/401,791

(22) Filed: Apr. 11, 2006

(65) Prior Publication Data
US 2007/0212791 A1 Sep. 13, 2007

Related U.S. Application Data

(60) Provisional application No. 60/784,623, filed on Mar. 10, 2006.

(51) Int. Cl.
*G01N 33/22* (2006.01)
*G01N 21/55* (2006.01)
*G01N 21/33* (2006.01)
*G01J 1/32* (2006.01)
*G01J 1/42* (2006.01)
*G01J 3/08* (2006.01)
*G01J 3/42* (2006.01)
*G01J 3/433* (2006.01)

(52) U.S. Cl. .................. 436/171; 250/372; 356/51; 356/217; 356/303; 356/319; 356/326; 356/447; 422/82.05; 422/82.09; 436/107; 436/110

(58) Field of Classification Search ............... 250/372; 356/51, 217, 303, 319, 323, 326, 331, 447; 422/82.05, 82.09; 436/107, 110, 171, 183
See application file for complete search history.

(56) References Cited

U.S. PATENT DOCUMENTS 5,357,346 A 10/1994 Piekarski et al.

(Continued)

FOREIGN PATENT DOCUMENTS

GB 2297377 * 7/1996

(Continued)

OTHER PUBLICATIONS

Pristera, F. et al, Analytical Chemistry 1960, 32, 495-508.*

(Continued)

*Primary Examiner*—Arlen Soderquist
(74) *Attorney, Agent, or Firm*—Akerman Senterfitt; Gregory A. Nelson; Gregory M. Lefkowitz (57) ABSTRACT

A system and method for identifying explosive or other target materials includes the steps of irradiating a first location and a second location spaced apart from the first location from a sample suspected of including explosives with ultraviolet, visible or infrared light, measuring reflected light emanated from the first sample location ($R_1$) and reflected light emanated from the second sample location ($R_2$), and calculating a normalized difference in reflectivity ($\Delta R/\overline{R}$), wherein $\overline{R}=(R_1+R_2)/2$ is an average reflectivity. A differential reflection spectrum (DRS) is then generated for the sample where $\Delta R=R_2-R_1$ is the difference of the reflectivities of the first and the second sample location. One or more explosives if present are identified in the sample based on comparing the DRS for said sample to at least one reference DRS.

20 Claims, 5 Drawing Sheets

U.S. PATENT DOCUMENTS

| | | | |
|---|---|---|---|
| 6,061,141 A * | 5/2000 | Goldenberg et al. | ........ 356/437 |
| 6,343,534 B1 | 2/2002 | Khanna et al. | |
| 2004/0124376 A1 | 7/2004 | Ershov et al. | |
| 2005/0024199 A1 | 2/2005 | Huey et al. | |
| 2005/0207943 A1 | 9/2005 | Puzey | |
| 2006/0022140 A1 | 2/2006 | Connelly et al. | |

FOREIGN PATENT DOCUMENTS

| | | |
|---|---|---|
| GB | 2417554 | 3/2006 |
| WO | WO 2004/083796 | 9/2004 |

OTHER PUBLICATIONS

Chance, B. et al, Review of Scientific Instruments 1963, 34, 1307-1311.*
Sell, D. D., Applied Optics 1970, 9, 1926-1930.*
McIntyre, J. D. E. et al, Surface Science 1971, 24, 417-434.*
Batz, B., Journal of Physics E: Scientific Instruments 1976, 9, 76-78.*
Wolterbeek, L. et al, Surface Science 1985, 152-153, 1071-1078.*
Selci, S. et al, Journal of Vacuum Science & Technology A 1987, 5, 327-332.*
Gal, M. et al, SPIE 1990, 1286, 136-145.*
Hummel, R. E., SPIE 1990, 1286, 146-153.*
Burns, T. M. et al, Journal of Vacuum Science & Technology B 1993, 11, 78-85.*
Kim, S. et al, Journal of Physical Chemistry B 1997, 101, 2735-2740.*
Kaur, M. et al, Current Topics in Forensic Science, Proceedings of the Meeting of the International Association of Forensic Sciences, 14th, Tokyo, Aug. 26-30, 1996 (1997), vol. 4, 228-234, Editors: Takatori, T. et al, Publisher: Shunderson Communications, Ottawa, Ont.*
Arbuthnot, D. et al, SPIE 1998, 3392, 432-440.*
MacCrehan, W. A. et al, SPIE 1999, 3576, 116-124.*
Zha, F. X. et al, Review of Scientific Instruments 1999, 70, 1798-1800.*
Moore, D. S., Review of Scientific Instruments 2004, 75, 2499-2512.*
Proehl, H. et al, Physical Review B 2005, 71, 165207/1-165207/14.*
Fitch, M. J. et al, SPIE 2005, 5790, 281-288.*
Skorpikova, M., New Trends in Research of Energetic Materials, Proceedings of the Seminar, 8th, Pardubice, Czech Republic, Apr. 19-21, 2005, vol. 2, 810-815, Editor: Vagenknecht, J., Publisher: University of Pardubice, Pardubice, Czech Rep.*
Hummel, R. E. et al, Applied Physics Letters 2006, 88, 231903/1-231903/3.*
Aspnes, D. E., IEEE Journal of Quantum Electronics 1989, 25, 1056-1063.*
Nee, T. W. et al, Journal of Applied Physics 1990, 68, 5314-5317.*
Rodriguez, R. et al, Journal of Colloid and Interface Science 1996, 177, 122-131.*
Henderson, G. Journal of Chemical Education 1999, 76, 868-870.*
Gal, M. SPIE 2001, 4594, 128-138.*
Yu, G. et al, Applied Physics Letters 2003, 83, 3683-3685.*
Tucks, A. et al, Journal of Solid State Chemistry 2005, 178, 1145-1156.*
Borensztein, Y. Physica Status Solidi A 2005, 202, 1313-1324.*
Hummel, R.E. "Differential Reflectometry and Its Application to the Study of Alloys, Ordering, Corrosion, and Surface Properties", Phys. Stat. Sol. (a), vol. 76, No. 11, 1983, pp. 12-44.
Hummel, R.E. "Differential Reflectance Spectroscopy in Analysis of Surfaces", Encyclopedia of Analytical Chemistry Ed. R.A. Meyers Chichester: John Wiley & Sons Ltd., 2000, pp. 9047-9071.
Felt et al. "UV-VIS spectroscopy of 2,4,6-trinitrotoluene-hydroxide reaction", Chemosphere, vol. 49, 2002, pp. 287-295.
Abe, T. "Ultraviolet Absorption Spectra of Nitro-, Dinitro- and Trinitro-substituted Benzenes", Bulletin Chem. Soc., 1958, vol. 31, No. 8, pp. 904-907.
Holbrook et al. "A 'Differential Relectometer' for Measurements of Small Differences in Reflectivity", The Review of Scientific Instruments, 1973, vol. 44, No. 4, pp. 463-466.
Hummel et al. "Optical Reflectivity Measurement on Alloys by Compositional Modulation", Physical Review Letters, 1970, vol. 25, No. 3, pp. 290-292.

* cited by examiner

FIG. 5 ated from the second sample location ($R_2$), and calcu-
DIFFERENTIAL REFLECTION SPECTROSCOPY SYSTEM AND METHOD FOR DETECTING EXPLOSIVES AND OTHER TARGET MATERIALS

CROSS-REFERENCE TO RELATED APPLICATIONS

This application claims priority to U.S. Provisional Patent Application No. 60/784,623 entitled "DIFFERENTIAL REFLECTION SPECTROSCOPY FOR DETECTING EXPLOSIVES" which was filed on Mar. 10, 2006, and is incorporated by reference in its entirety into the present application.

STATEMENT REGARDING FEDERALLY SPONSORED RESEARCH OR DEVELOPMENT

The United States Government has certain rights to the invention pursuant to Army Research Laboratory Grant No. DAAD 9-03-2-0004.

FIELD OF THE INVENTION

The invention relates to a spectroscopy system and method for the detection of target materials. More particularly, the invention relates to reflection and/or a differential reflection spectroscopy system and method for the detection of target materials including explosives and drugs.

BACKGROUND

The detection of traces of explosive materials is of utmost importance at the present time due to the ongoing risk of terrorism. Detection devices should identify explosives before detonation of the explosive and thus save lives. The technique for detecting such materials should be fast, portable, contact-less, inexpensive, foolproof, and reliable for maximum effectiveness.

A number of methods for detection of explosives have been proposed or are already in service. Non-portable instruments for explosives detection include gas chromatography (involving an electron capture detector), ion mobility spectrometers, mass spectrometers (detecting different masses of ions, separated in a magnetic field after heating the specimen), neutron analysis (based on neutron excitation of atoms in explosives), nuclear quadrupole resonance, and x-ray detection. Optical techniques include transmission measurements of explosives contained in solutions, or in the gaseous state in the ultraviolet, visible, or infrared range, fluorescence spectroscopy (coupled with immunoassay reactions whereby the explosive fluoresces when in contact with a sensor), quenching of photoluminescence (of an appropriate inert material by an explosive vapor), and photofragmentation (by separating $NO_2$ into O and NO by a laser followed by detection of NO using laser-induced fluorescence). Among the portable detectors are calorimetric detection devices (involving for example alkali-based chemicals which change color when they are exposed to certain types of explosives). A dog trained to detect explosive vapors can also be effective.

Although several methods are available for detecting explosives, a new, relatively simple, real-time, portable, high sensitivity and particularly, a stand-off technique that requires little or no sample preparation is needed.

SUMMARY

A method for identifying explosive materials includes the steps of irradiating a first location and a second location spaced apart from the first location from a sample suspected of including explosives with at least one of ultraviolet, visible, and infrared light, measuring reflected light emanated from the first sample location ($R_1$) and reflected light emanated from the second sample location ($R_2$), and calculating a normalized difference in reflectivity ($\Delta R/\bar{R}$), wherein $\bar{R}=(R_1+R_2)/2$ is an average reflectivity. A differential reflection spectrum (DRS) is then generated for the sample where $\Delta R=R_2-R_1$ is the difference of the reflectivities of the first and the second sample location. One or more explosives, if present, are identified in the sample based on comparing the DRS for said sample to at least one reference DRS. The identification can be from a distance. The target material on the sample can be a solid material. There is no need for any processing of the sample material to implement the method.

The method can comprise the step of collecting the sample from a region of interest suspected of containing explosives. In some embodiments the collecting step can include air filtration by applying a vacuum.

Explosives identifiable by the present invention includes at least nitroaromatics, nitroamines, nitroanilines and nitrates. The nitroaromatic can be selected from the group consisting of 1,4-dinitrobenzene, 2,4-dinitrotoluene, 2,6-dinitroluene, 1,3-dinitrobenzene, 4-nitrotoluene, and 2,4,6-trinitrotoluene, while the nitroamine can be selected from the group consisting of 1,3,5-trinitro-1,3,5-triazacyclohexane (RDX) and 1,3,5,7-tetranitro-1,3,5,7-tetrazacyclooctane (HMX), said nitroaniline is 2,4,6,N-tetranitro-N-methylaniline (Tetryl),and said nitrate from the group consisting of nitroglycerin, ammonium nitrate and ful oil (ANFO), and pentaerythritol tetranitrate (PETN).

The incident light can be provided by a plurality of monochromatic sources having different emission wavelengths or a broadband radiation source. In one embodiment, incident light is provided by a white light source and a charge coupled device (CCD) is used for the detection. The identifying step can comprise automated curve recognition.

A system for identifying explosives and other target materials comprises an ultraviolet, visible or infrared broadband light source for irradiating a first location and a second location spaced apart from the first location from a sample suspected of including explosives. A photodetector is provided for measuring reflected light emanated from first sample location ($R_1$) and reflected light emanated from the second sample location ($R_2$). A computer or processor having an associated memory is coupled to said photodetector, the computer or processor running software for calculating a normalized difference in reflectivity ($\Delta R/\bar{R}$), wherein $\bar{R}=(R_1+R_2)/2$ is an average reflectivity, generating a differential reflection spectrum (DRS) for said sample where $\Delta R=R_2-R_1$ is the difference of the reflectivities of the first and second sample location, and identifying one or more explosives if present in the sample based on comparing the DRS for the sample to at least one reference DRS stored in the memory.

The system can include an oscillating mirror for directing the radiation from the light source between the first location and the second location. In one embodiment, the system includes a monochromator in optical alignment with light from the light source, wherein the computer or processor is communicably connected to the monochromator. In this embodiment, the detector preferably comprises a photomultiplier tube. In another embodiment which does not require a monochromator, the light source is a white light source and the detector is a CCD.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION

A method for identifying target materials including explosives comprises using either straight reflectivity or differential reflectivity. According to various embodiments, differential reflectivity (DR) can be used to provide a higher sensitivity and pronounced spectral features from a target material when compared to straight reflectivity because DR yields the first derivative of the straight spectral reflectivity. DR comprises the steps of irradiating a first location of a sample suspected of including explosives with UV, visible, or infrared incident light, and measuring the difference of the spectrum of the reflected light emanated from a first sample location ($R_1$) and reflected light emanated from a second sample location ($R_2$). A normalized difference in reflectivity ($\Delta R/\overline{R}$) is then calculated and a differential reflection spectrum (DRS) is generated therefrom, where $\Delta R=R_2-R_1$ is the difference of the reflectivities of the first and second sample location, and $\overline{R}=(R_1+R_2)/2$ is an average reflectivity. One or more explosives or other target materials are then identified if present in the sample. In some embodiments, this can be performed automatically, based on comparing the DRS for the sample to at least one reference DRS.

Although generally described for the detection and identification of the explosive TNT, the invention can be used to detect and identify a variety of other explosives, as well as drugs, chemical poisons, or other controlled or illegal materials. The target material can be a nitroaromatic, such as 1,4-dinitrobenzene, 2,4-dinitrotoluene, 2,6-dinitroluene, 1,3-dinitrobenzene, 4-nitrotoluene, and 2,4,6-trinitrotoluene (TNT), or a nitroamine such as 1,3,5-trinitro-1,3,5-triazacyclohexane (RDX) and 1,3,5,7-tetranitro-1,3,5,7-tetrazacyclooctane (HMX). Also included are 2,4,6,N-tetranitro-N-methylaniline (Tetryl), nitroglycerin, ammonium nitrate and fuel oil (ANFO), and pentaerythritol tetranitrate (PETN). The target material is generally not chemically bound to the sub The DRS method of detection described herein is fast, inexpensive, reliable, portable, and does not require contact with the surveyed substance. Moreover, an automated curve recognition program can be provided for field applications of the invention.

Differential reflection spectroscopy, also called differential reflectometry (DR), is a surface analytical technique. DR uses light (UV, visible or infrared) as a probing medium and reveals details about the electron structure around the Fermi surface. Specifically, DR measures the energies that electrons absorb from photons as they are raised into higher, quantized energy states. Since each material has a specific electron structure, due to electron bands or electron levels stemming from molecular orbitals, the measurement of the characteristic energies for "electron transitions" allows positive identification of these materials. Essentially, the differential reflectometer yields the imaginary part of the complex dielectric constant $\epsilon_2=2nk$ (often called the absorption) as a function of the excitation wavelength (or equivalently, frequency or energy).

Differential reflectometry is a known technique to gain information about the absorption behavior of ultra-thin films on opaque substrates. (see Hummel, R. E. "Differential Reflectometry and its application to the study of alloys, ordering, corrosion, and surface properties." Phys. Stat. Sol. (a) Vol. 76, (1983), 11-44, Hummel, R. E. "Differential Reflectance Spectroscopy in analysis of surfaces." *Encyclopedia of Analytical Chemistry* Ed. R. A. Meyers Chichester: John Wiley & Sons Ltd., (2000) 9047-9071., Hummel, R. E, Dove, D. B., and Holbrook, J. A. "Optical reflectivity measurements on alloys by compositional modulation." Phys. Rev. Lett., 25 (1970) 290, and Holbrook, J. A. and Hummel, R. E. "A 'Differential Reflectometer' for measurements of small differences in reflectivity." Rev. Sci. Inst., 44 (1973) 463). Since many substrates are optically too thick to perform transmission measurements, the reflection signal is used instead, which indirectly contains the absorption properties of the target material.

The two sampled parts used for DR can comprise two different locations suspected of having the target material on the substrate. In another embodiment, where the sample is very thin, the bare substrate without the sample film is compared to the sample film on the substrate. The differential reflectometer thus measures the normalized difference between the reflectivities of two adjacent parts of the same or different specimen.

Figure 1:
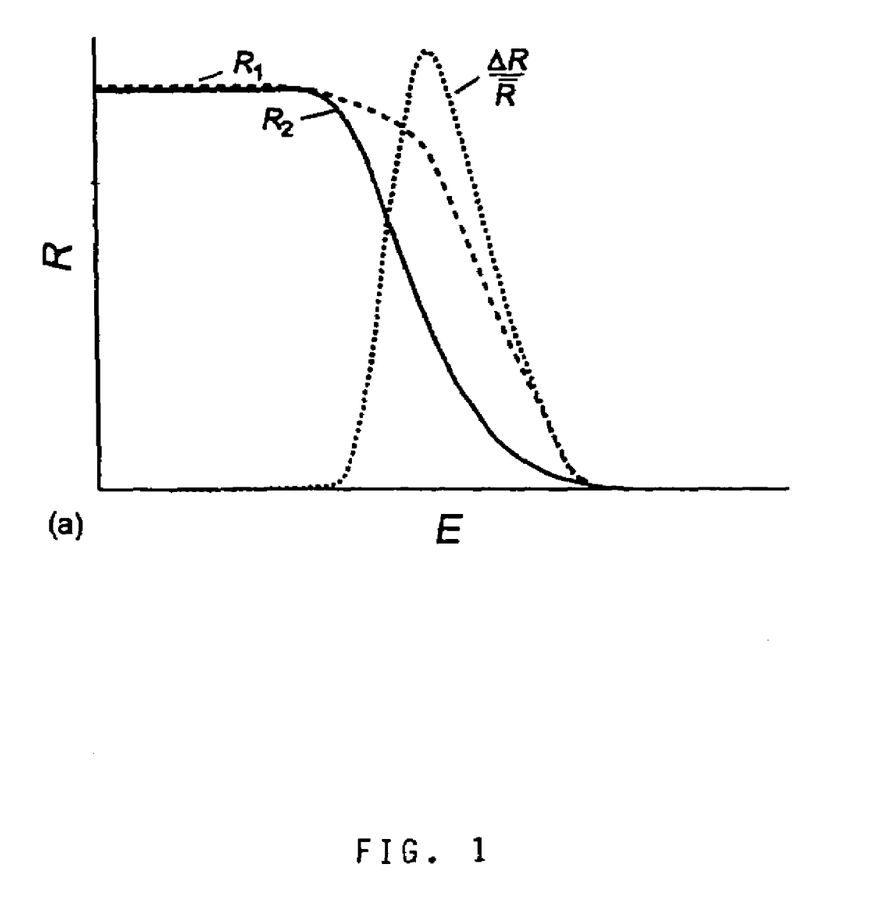
FIG. 1 is a schematic representation showing the advantage in sensitivity obtained by using a differential reflection spectrum (DRS) for a sample ($\Delta R/\overline{R}$), wherein $R=(R_1+R_2)/2$ is an average reflectivity of sample location ($R_1$) and second sample location ($R_2$), and $\Delta R=R_2-R_1$ is the difference of the reflectivities of the first and second sample location, as compared to the straight spectral reflectivity from the first sample location ($R_1$) and second sample location ($R_2$).

FIG. 1 clearly demonstrates the higher sensitivity and pronounced spectral features provided by the DR technique when compared to straight reflectivity. The reflected signal from the first sample location is $R_1$, and from the second sample location is $R_2$. $\Delta R/\overline{R}$ is the normalized difference in reflectivity, where $\Delta R=R2-R1$, and $\overline{R}=(R1+R2)/2$.

Figure 2:
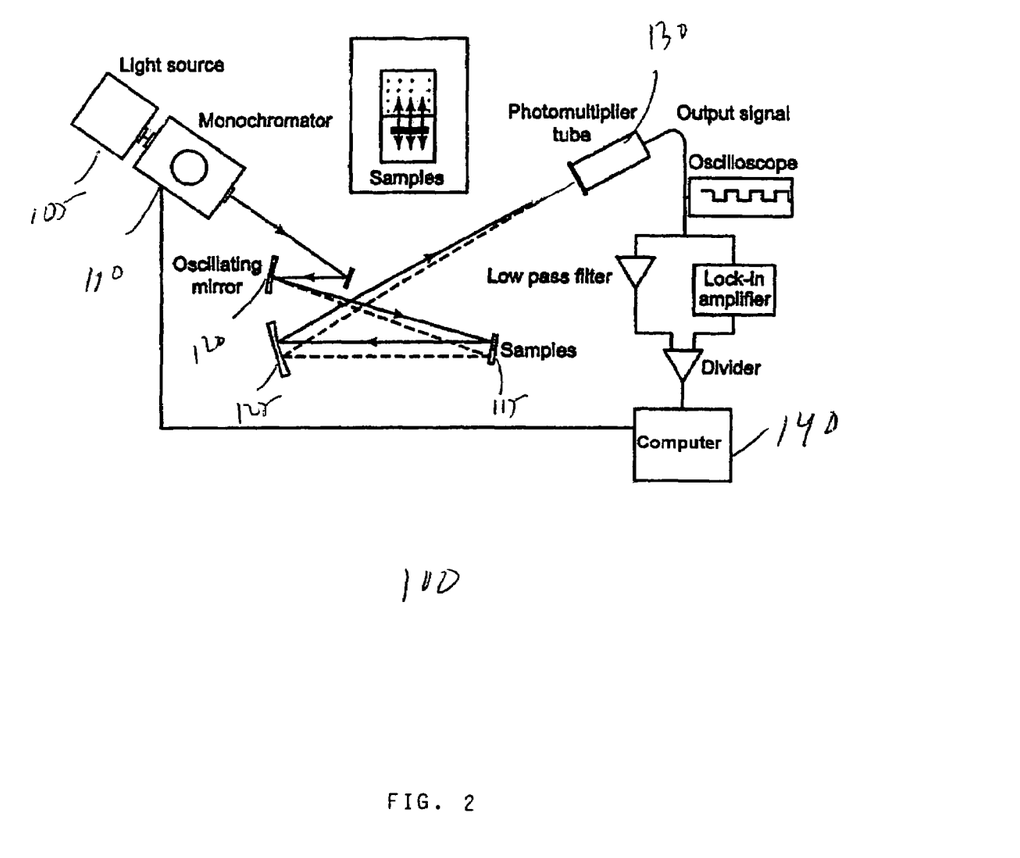
FIG. 2 is a schematic of an exemplary differential reflection spectrometer.

FIG. 2 is the schematic of an exemplary differential reflection spectrometer 100 which can be used with the invention. A broadband light source, such as a high pressure xenon source 105 or white light source, illuminates a monochromator 110 to provide monochromatic light having a continuously varying wavelength. The light is alternately deflected to one or the other part of the sample or samples 115 using an oscillating mirror 120. The total area scanned is generally about 2×4 mm². A stationary mirror 125, which is placed after the specimen, focuses the reflected light on the face of a photomultiplier (PMT) 130. In certain embodiments, PMT 130 is replaced by another detector, such as a charge coupled device (CCD). The output voltage from photomultiplier 130 is electronically processed, for example, by a computer 140, to yield the normalized difference in reflectivity, that is, $\Delta R/\bar{R}$ where $\Delta R = R_2 - R_1$ is the difference of the reflectivities of the two sample parts, and $\bar{R} = (R_1 + R_2)/2$ is the average reflectivity. Computer 140 also controls the operation of monochromator 110. In another embodiment a lock-in amplifier in conjunction with a differencing and dividing circuit can be utilized for a similar purpose.

Measuring $R_1$ and $R_2$ at essentially the same time and forming the ratio $\Delta R/\bar{R}$ eliminates possible influences from fluctuations of the line voltage. It also essentially eliminates intensity variations of the spectral output of the light source, the spectral sensitivity of the detector, and the spectral reflectivities of the mirrors or reflectivities from the substrate which generally underlies the sample 115. Thus, the sensitivity of the spectrometer 100 is quite high, in that the minimal measurable $\Delta R/\bar{R}$ is, as a rule, about 0.01%. In some embodiments, a white light source is used without a monochromator and PMT 130 is replaced by a CCD, thus accelerating the data acquisition.

Regarding an exemplary method, a DR system scans an area that may contain a small amount of target material, such as molecules, a particle, gases, vapors, and/or liquids of the explosive material. In various embodiments, an area is surveyed with a broadband light source and the differential reflection or straight reflection of the sample is recorded by a total spectral analysis detector, such as a CCD camera. If the reflection spectrum includes the spectral line shape within predetermined limits of the characteristic explosive material, then it is concluded that the area contains explosive materials or was exposed to explosive material.

Alternatively, the sample can be collected. Besides a direct measurement, as described above, various other embodiments can be used to collect a sample. In one example, a filter can be placed near a vacuum nozzle. For example, the nozzle can be inserted into the area under investigation and a quantity of air is forced through the filter. Particles and/or molecules in the air are trapped by the filter. The filter can then be placed in a differential reflectometer and the spectrum can be taken. Alternatively, a swab, can be brushed over the area. Particles and/or molecules will be picked up by the swab. The swab can then be placed in a DR arrangement and a spectrum can be taken.

According to various embodiments, any method that uses the absorption characteristics of an explosive material in the ultraviolet and/or the visible portion of the light spectrum can be used for their detection. For example, this method can examine an area possibly containing an explosive material with one or multiple light sources. According to certain embodiments, the light source can emit light in the range of about 200 nm to about 500 nm. Absorption characteristics for the sample area are obtained and the presence of an explosive material is determined using the absorption characteristic of explosive materials. For example, it has been found that explosive materials irradiated with a light source as described herein yield a characteristic absorption spectrum in the range of about 200 nm to 500 nm. This characteristic absorption spectrum can be used as a fingerprint to identify explosives or other target materials. The absorption characteristics of the explosive materials are based on detected spectra, such as those acquired by DR. This method can use all exemplary methods for sample collection.

According to certain embodiments, straight reflectivity can be used to detect explosive materials. In this case, the ratio between the reflected intensity and the emitted intensity is formed and displayed as a function of the incoming wavelengths. For example, a light source emitting light in the range of about 200 nm to about 500 nm is directed at a sample suspected of having the target material. The light is reflected from the sample and its intensity is measured with a photosensitive device and is set in relation to the incoming intensity.

The invention is expected to have a wide variety of applications and be particularly useful when high throughput and non-contact methods are required. For example, the invention can be used in a non-invasive manner in a variety of field environments for fast and reliable detection and identification of explosives and controlled substances. For example, the invention can enhance homeland security through sensitive detection of the presence of TNT or other explosives on an object, such as a suitcase, a vehicle, or a building from a distance without touching the suspected area. Products based on the invention can include explosive detection systems for use by police and other security authorities for protecting infrastructure, such as from possible terrorism. Systems according to the invention can also be used in airports, buildings, and in other areas where a bomb could be placed.

An important feature of the invention is that each explosive is distinguished by its characteristics DRS so that a positive identification of the specific explosive present can be made rather than just signaling the presence of nitrogen-containing compounds as provided by many prevailing technologies commonly in use.

EXAMPLES

It should be understood that the Examples described below are provided for illustrative purposes only and do not in any way define the scope of the invention.

Small quantities of 2,4,6-Trinitrotoluene (TNT), (containing a minimum of 30% water, purity 98%, rest Dinitrotoluene (DNT), no taggants, from Chem Service Inc), were dissolved in acetonitrile and then deposited on a carefully cleaned glass substrate. After evaporation of the volatile acetonitrile, the TNT monoclinic and/or orthorhombic crystals (dendritic needles) were scraped off and deposited on a black substrate (commercial SEM carbon pad). In a few cases TNT from the same source as mentioned above was investigated, but was dissolved instead in ethanol or acetone with subsequent crystallization. Undissolved, that is, as received, solid TNT (from Chem Service Inc and from the Alachua County Sheriffs Office) was also investigated. All cases yielded the same results shown in FIG. 3.

Figure 3:
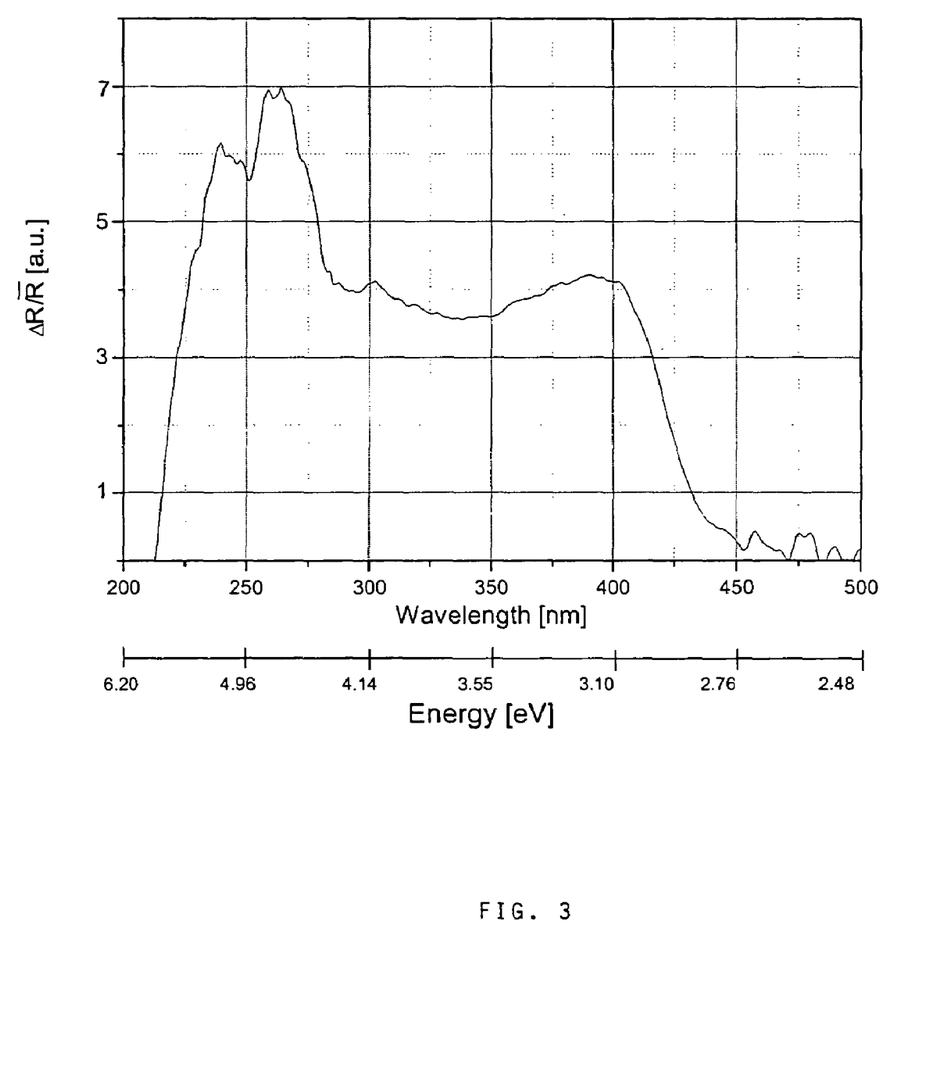
FIG. 3 is a differential reflectogram obtained from TNT crystals deposited on carbon tape.

FIG. 3 depicts a characteristic differential reflectogram (which displays $\Delta R/\bar{R}$, versus the excitation wavelength, see above) for solid, crystalline, pure TNT. It is observed that with decreasing wavelength (increasing excitation energies) $\Delta R/\bar{R}$ begins to gradually rise at about 435 nm and reaches a plateau near 400 nm. This structure is hereafter referred to as the "420 mm absorption". A second structure is detected in the form of a peak near 250 nm. In many cases (but not in all) this structure manifests itself as a double peak near 245 nm and 255 nm. Finally, a weak peak near 303 nm which overlaps the plateau is discernible. The 420 nm and the 250 nm structure have also been observed in transmission measurements for solutions of TNT in acetonitrile, as will be shown below.

The spectral onset of absorption, as seen at 435 nm in FIG. 3, is a well-known feature in insulators and particularly in semiconductors, that is, in solids that exhibit a band gap. While not intending to be limited with regard to theory, theory not being necessary to practice the invention, it is believed that this indicates that the threshold energy at which interband transitions set in. For single molecules (e.g. gases) and very diluted solutions of molecules the just-mentioned electron bands transform into energy levels thought to be associated with molecular orbitals and are referred to as HOMO-LUMO (Highest Occupied Molecular Orbital to Lowest Unoccupied Molecular Orbital) transitions. The appearance of several absorption peaks or shoulders for such "chromophores" is common for highly conjugated systems, that is, for molecules having alternating single, double, or triple bonds. Increasing multiple bonds brings the HOMO and LUMO orbitals closer together which causes a red-shift of the threshold energy (wavelength).

Figure 4:
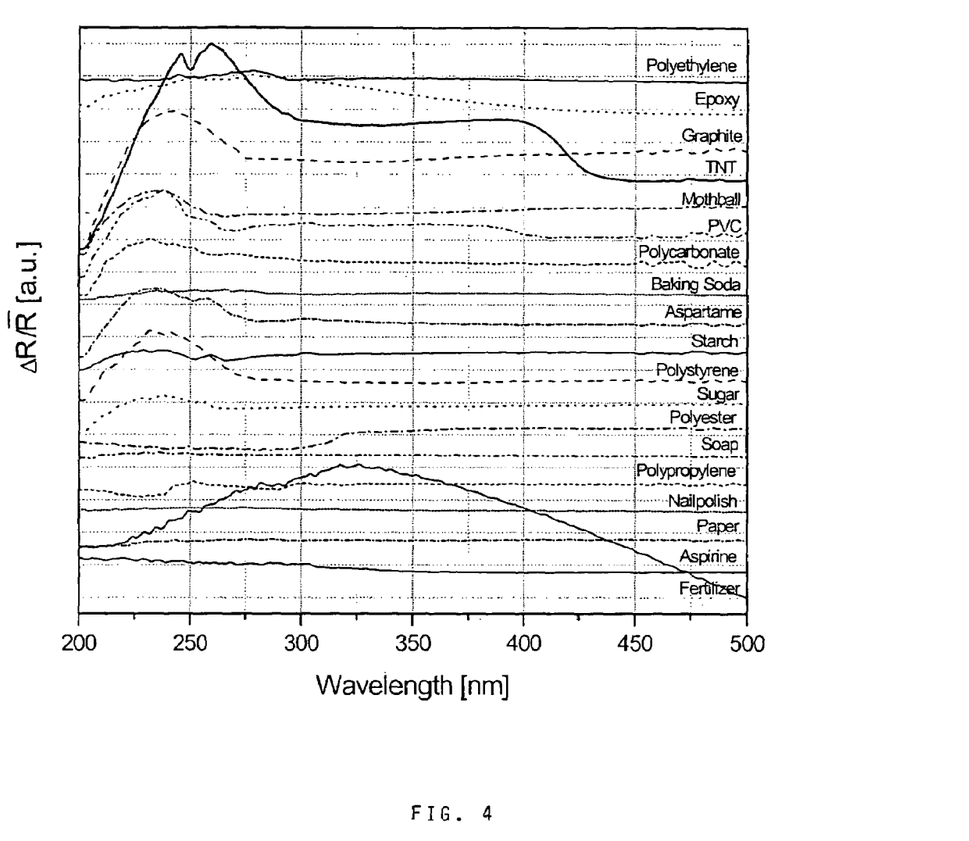
FIG. 4 shows differential reflectograms obtained from various substances in comparison to TNT. The individual curves have been staggered for clarity.

FIG. 4 depicts differential reflection spectra of a large number of mostly organic substances which could be expected to be found in or on the luggage of an average traveler. It is noted that none of these spectra have all the same features as TNT. In particular, the 420 nm structure is generally missing. In addition, the peak or peaks near 250 nm, observed for TNT is absent. Instead, absorption peaks are seen which are situated at higher or lower wavelengths. As an example, the spectrum for aspartame has a threshold wavelength near 260 nm and an absorption peak near 230 nm.

To complement and confirm the differential reflectometry data, transmission measurements of TNT dissolved in acetonitrile were collected utilizing four different UV-Vis spectrophotometers (Hitachi, Varian, Perkin-Elmer, Cary) which are double beam transmission instruments in which both the solvent and the solution to be investigated are inserted in two separate, but identical, quartz cuvettes of 1 cm width. These instruments yield the spectral absorbance of a substance, rather than $\epsilon_2$, that is, absorption.

Figure 5:
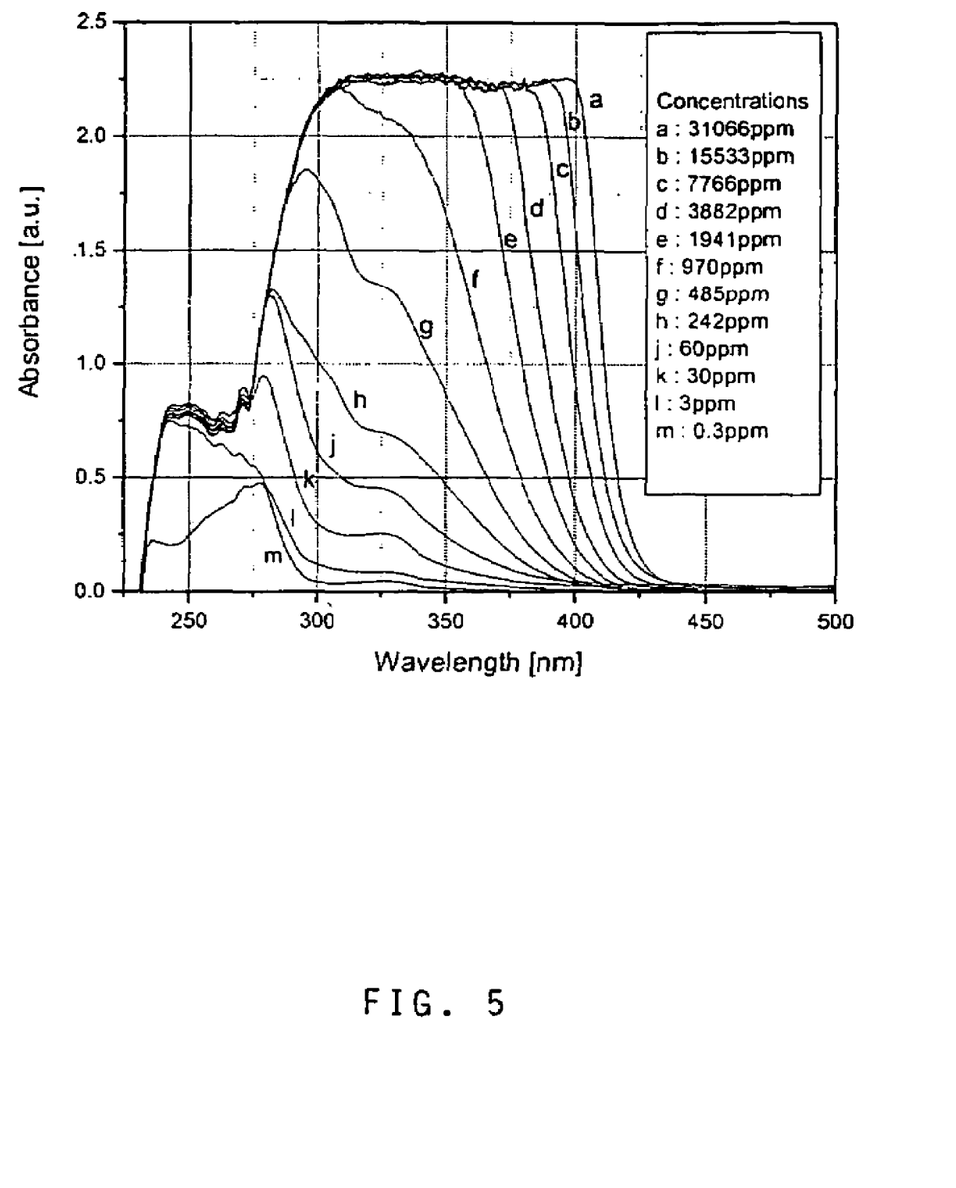
FIG. 5 depicts absorbance spectra taken in transmission mode involving various concentrations of TNT dissolved in acetonitrile.

In order to compare differential reflection according to the invention with transmission measurements (which are commonly found in the literature), TNT was dissolved in acetonitrile and the concentrations varied over six orders of magnitude. FIG. 5 shows the results when using a Hitachi spectrophotometer. As can be seen, the threshold energy for interband transitions for the highest concentration is situated at about the same wavelength (near 420 nm), as in FIG. 3. With increasing dilution this spectral threshold absorbance becomes flatter in shape until eventually a peak maximum is discernible and the overall absorbance decreases. The curve indicating a 0.3 ppm concentration of TNT in acetonitrile can be considered to essentially represent the absorbance from isolated molecules of TNT. This shift of the threshold energies seen in FIG. 4 shows the transition from essentially the solid state of TNT to an isolated TNT molecule.

Structures similar to those seen in FIGS. 3 and 5 were observed in transmission data by Felt et al. (Felt, D., Larson, S., and Valente, E. "UV-VIS spectroscopy of 2,4,6-trinitrotoluene-hydroxide reaction", Chemosphere 49 (2002): 287-295) when using a mixture of TNT, water, and KOH. Specifically, weak shoulders near 254 nm and 280 nm were reported. Similarly, for TNT in various solutions (such as water, ethanol, benzene, or acetone) Abe (Abe, T, "Ultraviolet Absorption Spectra of Nitro-Dinitro- and Trinitro-substituted Benzenes", Bulletin Chem. Soc. Japan. 31 (1958): 904-907) observed a weak absorbance shoulder near 300 nm and a peak near 225 nm using a Hitachi transmission spectrophotometer. However, Felt et al. and Abe have dissolved TNT in a solution. Further, neither Felt et al. nor Abe resolved a pronounced characteristic spectrum for TNT as seen in FIG. 3. Most of all, however, Felt et al. and Abe performed their experiments in transmission utilizing a dilute solution. As such, their techniques are impractical for routine screening.

Although taggants added by the manufacturer to the TNT could provide the described structures for TNT, no taggants were present in the substances used based on information provided by the supplier. It could be further argued that the structure could stem from the black carbon pad which is used as substrate. However, transmission measurements, which do not involve carbon tape, showed the same peaks or structure, as mentioned above. Further, differential reflectograms of the carbon tape only, does not show any structure.

In order to discriminate between TNT and other organic substances, a curve discrimination program was developed based on the LabVIEW software (National Instruments). An average spectral distribution was derived from the $\Delta R/\overline{R}$ of several different TNT samples. The spectrum from an "unknown" sample was normalized to the average TNT spectrum and an envelope region having an upper 5% and a lower 5% deviation was utilized as the comparative standard. This normalization procedure was done in order to not exclude weaker reflectors. The program has been shown to reliably detect TNT and discriminate other substances. Moreover, differential reflectograms of TNT on materials such as leather or fabric, show the same structure as described above.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. A method for identifying explosive materials, comprising the steps of:

irradiating a first location and a second location of a sample suspected of having one or more target materials deposited thereon with a broadband light source emitting light in the range of 200 nm to 500 nm, said second sample location spaced apart from said first sample location, wherein the target materials comprise one or more explosive comprising materials, exclusive of liquid solvents having one or more solutes comprising explosive materials;

measuring reflected light emanated from said first sample location ($R_1$) and reflected light emanated from said second sample location ($R_2$);

generating a differential reflection spectrum (DRS) for said sample by calculating a normalized difference in reflectivity of said first and said second sample locations ($\Delta R/\overline{R}$), wherein $\Delta R=R_2-R_1$ is the difference of the measured reflected light from said first and said second sample locations, and wherein $\overline{R}=(R_1+R_2)/2$ is an average reflectivity of said sample; and identifying said one or more explosives or other target materials if present on said sample based on comparing said generated DRS to at least one reference DRS for said one or more explosives or other target materials.

2. The method of claim 1, further comprising the step of preparing said sample by depositing thereon materials collected from a region of interest suspected of containing said explosives.

3. The method of claim 2, wherein said preparation step comprises air filtration by applying a vacuum.

4. The method of claim 1, wherein said explosive materials include at least one nitro aromatic, nitroamine, nitroaniline, or nitrate.

5. The method of claim 4, wherein said nitroaromatic is selected from the group consisting of 1,4-dinitrobenzene, 2,4-dinitrotoluene, 2,6-dinitrotoluene 1,3-dinitrobenzene, 4-nitrotoluene, and 2,4,6-trinitrotoluene.

6. The method of claim 4, wherein said nitroamine is selected from the group consisting of 1,3,5-trinitro-1,3,5-triazacyclohexane (RDX) and 1,3,5,7-tetranitro-1,3,5,7-tetrazacyclooctane (HMX), said nitroaniline is 2,4,6,N-tetranitro-N-methylaniline (Tetryl), and said nitrate from the group consisting of nitroglycerin, ammonium nitrate and fuel oil (ANFO), and pentaerythritol tetranitrate (PETN).

7. The method of claim 1, wherein a spectrometer coupled to a charge coupled device (CCD) is used for said detection.

8. The method of claim 1, wherein said identifying comprises automated curve recognition.

9. The method of claim 1, wherein at least of said one or more explosives materials is identified if a shape of said generated DRS is within a deviation envelope for said at least one reference DRS.

10. The method of claim 9, wherein said shape comprises fitting a curve to said generated DRS.

11. The method of claim 1, further comprising repeating the steps of irradiating, measuring, generating, and identifying for one or more other samples in an area of interest.

12. The method of claim 1, wherein said first location and said second locations on said sample are irradiated by moving a beam path of said emitted light and the sample relative to each other.

13. The method of claim 12, wherein said moving comprises using an oscillating mirror to deflect said beam path between said first location and said second sample location.

14. A system for identifying explosive materials, comprising:

a broadband light source emitting light in the range of 200 nm to 500 nm for irradiating a first location and a second location of a sample surface suspected of having one or more target materials deposited thereon, said second sample location spaced apart from said first sample location, wherein the target materials comprise one or more explosive comprising materials, exclusive of liquid solvents having one or more solutes comprising explosive materials;

a photodetector for measuring reflected light emanated from said first sample location ($R_1$) and reflected light emanated from said second sample location ($R_2$), and a computer or processor having an associated memory coupled to said photodetector, said computer or processor running software for generating a differential reflection spectrum (DRS) for said sample by calculating a normalized difference in reflectivity ($\Delta R/\overline{R}$) of said first and said second sample locations, where $\Delta R = R_2 - R_1$ is the difference of the measured reflected light from said first and said second sample locations and $\overline{R} = (R_1 + R_2)/2$ is an average reflectivity of said sample, and for identifying said one or more explosives or other target material if present on said sample based on comparing said generated DRS to at least one reference DRS for said one or more explosives or other target materials stored in said memory.

15. The system of claim 14, further comprising an oscillating mirror for receiving light from said light source and alternately deflecting said light between said first and said second sample location.

16. The system of claim 14, further comprising a monochromator in optical alignment with light from said light source, computer or processor communicably connected to said monochromator, wherein said photodetector comprises a photomultiplier tube.

17. The system of claim 14, wherein said photodetector is a CCD.

18. The system of claim 14, wherein at least of said one or more explosive materials is identified if a shape of said generated DRS is within a deviation envelope for said at least one reference DRS.

19. The system of claim 18, wherein said computer or processor generates said shape by fitting a curve to said generated DRS.

20. The system of claim 14, wherein said computer generates said DRS in real-time.

* * * * *